United States Patent [19]

Reddy et al.

[11] Patent Number: 5,731,429
[45] Date of Patent: Mar. 24, 1998

[54] $C^{AC}$-METHYLPHOSPHONAMIDITES AND METHODS FOR PREPARING METHYLPHOSPHONATES

[75] Inventors: Meda Parameswara Reddy; Firdous Farooqui, both of Brea; Naeem B. Hanna, Fullerton, all of Calif.

[73] Assignee: Beckman Instruments, Inc., Fullerton, Calif.

[21] Appl. No.: 544,683

[22] Filed: Oct. 18, 1995

[51] Int. Cl.$^6$ .............................. C07H 1/02; C07H 19/20
[52] U.S. Cl. ............................... 536/25.34; 536/26.8
[58] Field of Search ........................ 536/25.34, 26.8

[56] References Cited

U.S. PATENT DOCUMENTS

| | | | |
|---|---|---|---|
| 5,348,868 | 9/1994 | Reddy et al. | 435/91.1 |
| 5,428,148 | 6/1995 | Reddy et al. | 536/26.8 |

OTHER PUBLICATIONS

Miller, Paul S.; "Oligonucleoside Methylphosphonates as Antisense Reagents", Biotechnology, vol. 9, Apr. 1991, pp. 358–362.

Miller, Paul S., et al; "Solid–Phase Syntheses of Oligodeoxyribonucleoside Methylphosphonates"; Biochemistry 1986, vol. 25, pp. 5092–5097.

Miller, Paul S. et al; "Preparation of Oligodeoxyribonucleoside Methylphosphonates on a Polystyrene Support"; Nucleic Acids Research, vol. 11, No. 18, 1983.

Hogrefe, Richard I, et al; "Deprotection of Methylphosphonate Oligonucleotides Using a Novel One-Pot Procedure"; Nucleic Acids Research, 1993, vol. 21, No. 9, pp. 2031–2038.

Agrawal, Sudhir, et al; "Oligodeoxynucleoside Methylophosphonates: Synthesis and Enzymic Degradation"; Tetrahedron Letters, vol. 28, No. 31, pp. 3539–3542, 1987.

Kandimalla, Ekambar R.; et al; "Synthesis and Properties of 2'–O–Methylribonucleotide Methylphosphonate Containing Chimeric Oligonucleotides"; Nucleosides & Nucleotides, 14(3–5), pp. 1031–1035 (1995).

Vaghefi, Morteza M., et al; "A Convenient High Yield Synthesis of N4–Isobutyryl-2'–o–Methylcytidine and Its Monomer Units for Incorporation into Oligonucleotides", Nucleosides & Nucleotides, 12(10), pp. 1007–1013 (1993).

*Primary Examiner*—Gary L. Kunz
*Attorney, Agent, or Firm*—William H. May; P. R. Harder; Sheldon & Mak

[57] ABSTRACT

A compound of general formula

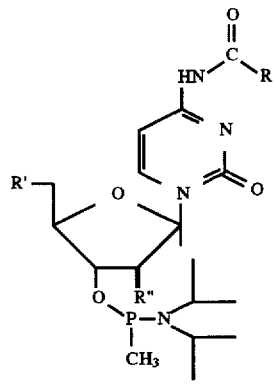

wherein R is methyl R' is selected from the group consisting of trityl and pixyl, and R" is H or OMe. These compounds may advantageously be employed in the synthesis of oligonucleotides by conventional methods, such as automated solid phase synthesis. Use of ethylene diamine in the cleavage and deprotection procedure substantially eliminates the formation of undesirable side products.

8 Claims, No Drawings

$C^{AC}$-METHYLPHOSPHONAMIDITES AND METHODS FOR PREPARING METHYLPHOSPHONATES

BACKGROUND OF THE INVENTION

The present invention relates generally to the fields of chemistry and biology. In particular, the present invention is directed to compositions and methods for use in oligonucleotide synthesis.

Oligonucleotides are short stretches of DNA or RNA, typically comprising up to about 100 nucleotides. In many instances, modified nucleotides may be employed in place of the naturally-occurring nucleotides. Oligonucleoside methylphosphonates, which possess a methyl phosphodiester linkage in the place of the phosphodiester linkage present in normal oligonucleotides, are among the most widely studied of the modified oligonucleotides [Miller, P. S., *Biotechnology* (1991) 9, 358–362; Miller, P. S. (1989) In Cohen, J. (ed.) *Oligonucleotides: Antisense Inhibitors of Gene Expression. Topics in Molecular and Structural Biology* 12, MacMillan Press, London, pp. 79–95; Miller, P. S. et al., *Biochemistry* (1986) 25, 5092–5097]. They satisfy the criteria of nuclease resistance, cell membrane permeability and affinity to a complementary nucleic acid strand. Further, oligonucleotides comprising oligonucleoside methylphosphonates may be synthesized using chemistries similar to those employed in the synthesis of conventional oligonucleotides (e.g., by a solid phase methodology).

The major difference between methods for the preparation of oligonucleotide methylphosphonates and those for preparation of standard oligonucleotides is in the cleavage and deprotection procedure. Whereas standard oligonucleotides are typically cleaved using ammonium hydroxide, the use of ammonium hydroxide in the cleavage and deprotection of oligonucleoside methylphosphonates results in a significant degradation of the methylphosphonate backbone.

In order to avoid undesirable degradation ethylene diamine/ethanol was developed as a more gentle and less destructive reagent [Miller, P. S. et al., *Nucleic Acids Research* (1983) 11, 6225–6242; Miller, P. S. et al., *Biochemistry* (1986) 25, 5092–5097]. A drawback with this approach, however, is that ethylene diamine produces as much as about 20% of a transamination side product with $N^4$-benzoyl cytidine.

In order to reduce this side product formation, $N^4$-isobutyryl protected cytidine has been employed [Hogrefe et al., *Nucleic Acids Research* (1993) 21, 2031–2038]. This reduces the amount of side product formation to about 2.9%. Although this reduction in side product formation is significant, it is highly desirable to reduce it even further.

It is an object of the present invention to provide compositions and methods which do not suffer from all the drawbacks of the prior art.

SUMMARY OF THE INVENTION

In accordance with the present invention, there are provided compounds of the general formula

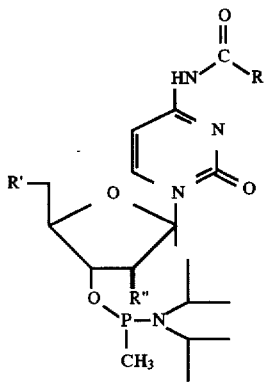

wherein R is alkyl of 1 to about 10 carbon atoms, R' is selected from the group consisting of trityl and pixyl, and R" is H or OMe. These compounds may advantageously be employed in the synthesis of oligonucleotides by conventional methods, such as automated solid phase synthesis. Use of ethylene diamine or a mixture thereof with a substantially inert solvent in the cleavage and deprotection procedure substantially eliminates the formation of undesirable side products.

DETAILED DESCRIPTION OF THE INVENTION

The present invention provides a solution to the problem of side product formation heretofore attendant to the synthesis of oligonucleoside methylphosphonates. Transamination problems observed with $N^4$-protected cytidine upon treatment with methylamine in the synthesis of conventional oligonucleotides have been addressed by the use of DMT $C^{Ac}$ phosphoramidite [Reddy, M. P. et al., *Tetrahedron Lett.* (1994) 25, 4311–4314; U.S. Pat. No. 5,348,868; U.S. Pat. No. 5,428,148]. The use of $C^{Ac}$ nucleoside with ethylene diamine reduced the formation of transamination side products to an extent such that in many instances side products were virtually undetectable. Prior to the present invention, however, it could not have been predicted whether or not the formation of undesired side products could be reduced in an analogous manner in syntheses involving the use of the structurally dissimilar methylphosphonates.

Pursuant to the present invention, 5'-DMT-$N^4$-acetyl deoxycytidine-3'-β-cyanoethyl-N,N-diisopropyl methylphosphonamidite ("$C^{Ac}$ methylphosphonamidite") of formula

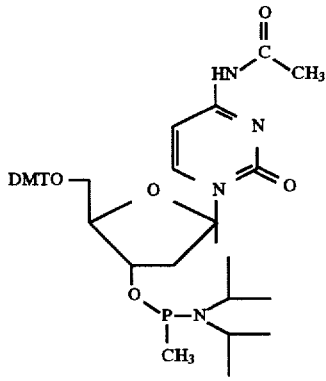

was synthesized as hereinafter described. The $C^{Ac}$ methylphosphonamidite was successfully employed in the synthesis of oligonucleoside methylphosphonates. In order to evaluate the extent of side product formation, dinucleotides containing the methylphosphonate linkage were synthesized. Side product formation was substantially reduced when C$^{Ac}$ methylphosphonamidite was employed in the synthesis.

In accordance with one particular preferred embodiment of the present invention, the 2'-OMe C$^{Ac}$ methylphosphonamidite of formula

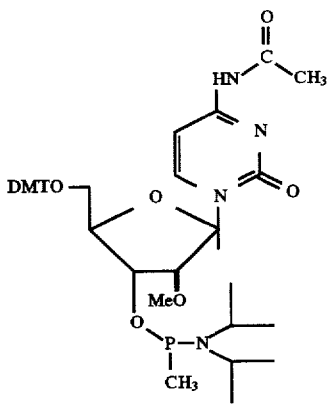

is provided. This compound was synthesized as hereinafter described. The introduction of the 2'-OMe group results in preparation of products which bind more strongly to complementary sequences. The C$^{Ac}$ protective group makes it possible to use ethylene diamine for cleavage without the formation of any significant amount of side products.

For purposes of the present invention, either neat ethylene diamine or a mixture of ethylene diamine and a substantially inert solvent (e.g., methanol, ethanol, acetonitrile, water, etc.) may be employed for cleavage and deprotection. Mixtures comprising about 10% to about 100% ethylene diamine are preferred.

The invention may be better understood with reference to the accompanying examples, which are intended for purposes of illustration only and should not be construed as in any sense limiting the scope of the instant invention as defined in the claims appended hereto.

EXAMPLE 1

C$^{Ac}$ methylphosphonamidite was synthesized as depicted below:

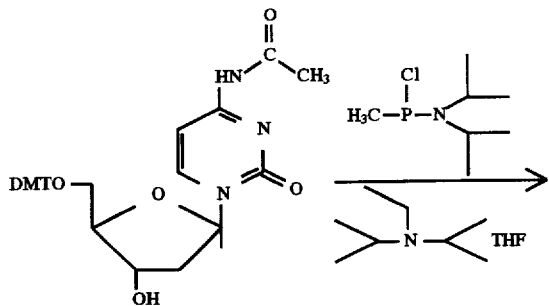

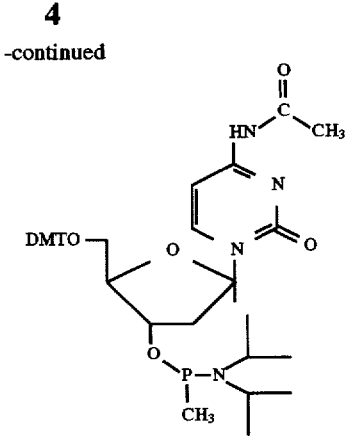

DMT C$^{Ac}$ (11.42 g, 20 mmoles) was dried by successive co-evaporations with pyridine, toluene and THF. The dried residue was dissolved in dry THF (100 ml) and redistilled N,N,N-diisopropylethylamine (17 ml, 80 mmoles) was added, followed by the addition of methylmonochloro-N,N-diisopropylphosphonamidite (10 ml) dropwise under argon over 5 minutes. After 16 hours of stirring, the reaction mixture was diluted with ethyl acetate (250 ml), washed with 10% NaHCO$_3$ solution (2×200 ml) and dried over Na$_2$SO$_4$. The crude material was dissolved in ethyl acetate and transferred to a silica gel column (2×30 cm, 70–230 mesh, 60 A, preheated at 100°–120° C. overnight). Elution with ethyl acetate gave the desired material. It was evaporated to dryness and was further dried under high vacuum for 5 hours to yield the phosphonamidite (8.5 g, 59% yield).

m.p.: 100°–110° C.
R$_f$=0.6 in CH$_2$Cl$_2$:MeOH (95:5, v/v)
UV (EtOH): λ max 298 nm, 283 nm and 236 nm
IR (KBr): v 1652 (vs, br, CO of amides), 1716 (s, CO of acetyl) and 3000–3100 (NH) cm-1.

$^1$H-NMR (CDCl$_3$): δ 0.86–1.27 (m, 15 H, P—CH$_3$ and C H$_3$ iPr), 2.25 (s, 3H, COCH$_3$), 2.28 and 2.70 (2 m, 2H, C$_2$, CH$_2$), 3.45 (m, 4H, C$_5$, CH$_2$, 2×CH iPr), 3.80 (s, 6H, 2×OC H$_3$ DMTr), 4.15 (m, 1H, C$_4$, H), 4.50 (m, 1H, C$_3$, H), 6.22 (2 t, 1H, C$_1$,H), 6.81–7.43 (m, 14 H, C$_5$H and aromatic protons of DMTr), 8.25 (2 d, 1H, C$_6$H) and 9.70 (br, s, 1H, NHCO).

$^{31}$P-NMR (CDCl$_3$): δ 121.15 ppm and 119.65 ppm.

Calcd. for C$_{39}$H$_{49}$N$_4$O$_7$P.2H$_2$O (752.78): C, 62.22; H, 7.10; N, 7.44; P, 4.11. Found: C, 62.40; H, 7.57; N, 7.02; P, 4.30.

HPLC: retention time of 15.34, corresponding to two diastereoisomers (99.344% purity). Conditions: C$_{18}$ Ultrasphere column (Beckman Instruments) 5µ particles, 4.6 mm×25 cm. Bottle A: 0.1M Ammonium acetate (pH 6.9); Bottle B: Acetonitrile. Program: Flow rate 1 ml/min. 0–20 min at 80% B.

EXAMPLE 2

A 21 mer methylphosphonate was synthesized using C$^{Ac}$ methylphosphonamidite, employing a procedure as described in the literature [Agarwal, S. & Goodchild, J., Tetrahedron Letters (1987) 28, 3539]. After synthesis, the oligonucleotide was cleaved and deprotected with 1 ml EDA/EtOH (1:1) for 7 hrs at room temperature. The product was analyzed by reverse phase HPLC and found to be substantially pure with essentially no detectable side products.

EXAMPLE 3

C$^{Ac}$, C$^{ibu}$ and C$^{bz}$ nucleoside were treated with ethylene diamine for 1–6 hours. The solvent was then completely evaporated. The residue was dissolved in water and subjected to reverse phase HPLC. The % of side product formed with each nucleoside is reported in Table 1.

Conditions for HPLC: $C_{18}$ Partisphere, Whatman column, 4.6 mm×25 cm. Bottle A: 0.1M ammonium acetate (pH 6.9), Bottle B: Acetonitrile. Program: Flow rate 1 ml/min, 0–20 min gradient to 15% B, 20–25 mins gradient to 25% B, 25–27 mins gradient to 50% B, 27–30 mins at 50% B, 30–35 mins at 0% B.

TABLE 1

| Substituted deoxycytidine | % of side product |
|---|---|
| $C^{Ac}$ | Not detected |
| $C^{ibu}$ | 2.90% |
| $C^{bz}$ | 22.33% |

EXAMPLE 4

CT methylphosphonate dimers were synthesized using $C^{Ac}$, $C^{ibu}$ and $C^{bz}$ methylphosphonamidite on T-CPG on a Beckman Oligo 1000 DNA synthesizer. The coupling time was 5 minutes. The product was cleaved and deprotected with ethylene diamine for 1 hour at room temperature. The solution was completely evaporated and the residue was dissolved in water and analyzed on HPLC. The conditions for HPLC are same as in Example 3. The % of side product in each case is given in Table 2.

TABLE 2

| Dimer (Methylphosphonate) | % of side product with ethylene diamine |
|---|---|
| $C^{Ac}T$ | Not detected |
| $C^{ibu}T$ | 4.616% |
| $C^{bz}T$ | 16.393% |

EXAMPLE 5

This example describes the synthesis of $N^4$-Acetyl-5'-O-(4,4'-dimethoxytrityl)-2'-O-methylcytidine-3'-(N,N-diisopropyl)-methylphosphonamidite. DMT-$N^4$-acetyl 2'-O-methylcytidine (0.6 g, 1 mmoles) was dried by successive coevaporations with pyridine, toluene and THF. The dried residue was dissolved in dry THF (5 ml) and redistilled N,N,N-diisopropylethylamine (0.8 ml, 4 mmoles) was added, followed by the addition of excess methylmonochloro-N,N-diisopropylphosphonamidite (0.6 ml) dropwise under argon over 5 minutes. After 16 hours of stirring, the reaction mixture was diluted with ethyl acetate (25 ml), washed with 10% $NaHCO_3$ solution (2×20 ml) and dried over $Na_2SO_4$. The crude material was dissolved in ethyl acetate and transferred to a silica gel column (2×30, 70–230 mesh, 60 A, preheated at 100°–120° C. overnight). Elution with ethyl acetate gave the desired material, which was evaporated to dryness and further dried under high vacuum for 5 hours to yield $N^4$-acetyl-5'-O-(4,4'-dimethoxytrityl)-2'-O-methylcytidine-3'-(N,N-diisopropyl)-methylphosphonamidite (0.37 g, 50% yield).

UV (EtOH): λ max 299 nm, 282 mn and 236 nm.

IR (KBr): v 1670 (vs, CO of ring amide), 1720 (s, CO of acetamide) and 3000 (br s, NH) cm-1

$^1$H-NMR (CDCl$_3$): δ 0.87–1.44 (m, 15H, P CH$_3$ and C HiPr), 2.22 (s, 3H, COCH$_3$), 3.40–4.47 (m, 16H, C$_5$CH$_2$, 2×CHiPr$_1$, 2'-OCH$_3$, 2×OCH$_3$, C$_{2',3',4'}$H), 5.96 and 6.08 (2 s, 1H, C$_1$·H), 6.81–7.49 (m, 14H, DMT aromatic protons and C$_5$H), 8.59 (d, 1H, C$_8$H), and 9.85 (br, s, 1H, NHCO).

$^{31}$P-NMR (CDCl3): δ 129.00 ppm and 122.26 ppm.

HPLC: Retention times of 9.45 and 11.69 corresponding to the two diastereoisomers (98% purity). Conditions: C18 Microsorb (Rainin column) S4 particles 4.6 mm×25 cm. Bottle A: 0.1 m ammonium acetate (pH 6.9). Bottle B: Acetonitrile. Program Flow rate 1 ml/min, 0–20 min at 80% B.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A compound of general formula

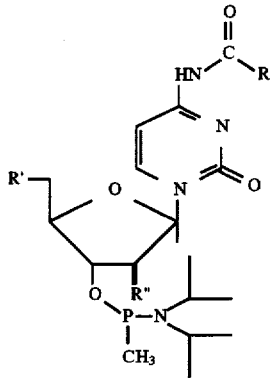

wherein R is methyl R' is selected from the group consisting of trityl and pixyl, and R" is H or OMe.

2. A compound according to claim 1, wherein R" is H.

3. A compound according to claim 1, wherein R" is OMe.

4. In a method of synthesizing oligonucleoside methylphosphonates by addition of nucleosides to a solid phase followed by deprotection and cleavage of a completed sequence from the solid phase, the improvement comprising use of a compound of general formula

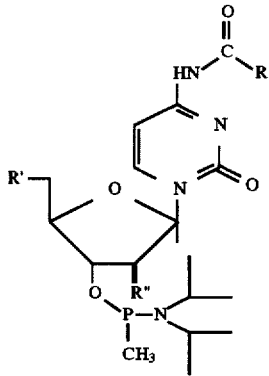

wherein R is methyl R' is selected from the group consisting of trityl and pixyl, and R" is H or OMe.

5. A method according to claim 4, wherein R" is H.

6. A method according to claim 4, wherein R" is OMe.

7. A method according to claim 4, wherein deprotection is effected using a reagent comprising ethylene diamine as active component.

8. A method according to claim 7, wherein a mixture of ethylene diamine and ethanol is employed comprising about 10% to about 100% ethylene diamine.

* * * * *